(12) United States Patent
Feldreich

(10) Patent No.: US 11,351,393 B2
(45) Date of Patent: Jun. 7, 2022

(54) APPARATUS FOR USE IN IRRADIATION THERAPY COMPRISING IONIZATION MODULE AND UV-LIGHT SOURCE

(71) Applicant: FELDREICH CARO RUIZ AB, Stockholm (SE)

(72) Inventor: Gustav Nicolas Feldreich, Stockholm (SE)

(*) Notice: Subject to any disclaimer, the term of this patent is extended or adjusted under 35 U.S.C. 154(b) by 0 days.

(21) Appl. No.: 16/093,642

(22) PCT Filed: Apr. 13, 2017

(86) PCT No.: PCT/SE2017/050374
§ 371 (c)(1),
(2) Date: Oct. 14, 2018

(87) PCT Pub. No.: WO2017/180054
PCT Pub. Date: Oct. 19, 2017

(65) Prior Publication Data
US 2019/0126057 A1     May 2, 2019

(30) Foreign Application Priority Data
Apr. 14, 2016   (SE) .................................. 1630088-1

(51) Int. Cl.
*A61N 5/06*     (2006.01)
*A61N 5/10*     (2006.01)
(Continued)

(52) U.S. Cl.
CPC .......... *A61N 5/062* (2013.01); *A61K 41/0057* (2013.01); *A61K 41/0066* (2013.01); *A61N 5/10* (2013.01); *A61P 11/00* (2018.01); *A61P 25/00* (2018.01); *A61P 35/00* (2018.01); *A61P 37/06* (2018.01); *A61L 2/08* (2013.01); *A61L 2/10* (2013.01); *A61N 2005/0661* (2013.01);
(Continued)

(58) Field of Classification Search
CPC .... A61N 5/064; A61N 5/0603; A61N 5/0616; A61N 2005/0602
See application file for complete search history.

(56) References Cited

U.S. PATENT DOCUMENTS

| | | | |
|---|---|---|---|
| 5,317,574 A * | 5/1994 | Wang | H05G 2/003 372/5 |
| 2003/0153961 A1 * | 8/2003 | Babaev | A61M 37/0092 607/89 |

(Continued)

*Primary Examiner* — Mallika D Fairchild
(74) *Attorney, Agent, or Firm* — Mark David Torche; Patwrite Law

(57) ABSTRACT

The present invention relates to an apparatus (1) for use in irradiation therapy, comprising an ionization module (2) adapted to emit ionization irradiation, and a power source (4) and a control unit (5) to provide a user interface. The apparatus is characterized in that the apparatus comprises an UV module (3) adapted to emit UVA, UVB and/or UVC irradiation (9), whereby the ionization module and the UV module emit irradiation simultaneously or alternately, and the ionization module emits irradiation (8) at a wave length at least below 100 nm. The invention also relates to a use of the apparatus for radiating an object (7) and use of the apparatus and method for treatment of a mammal (7). A detector may measure and/or create an image of the irradiation (6).

14 Claims, 5 Drawing Sheets

(51) Int. Cl.
*A61K 41/00* (2020.01)
*A61P 25/00* (2006.01)
*A61P 37/06* (2006.01)
*A61P 35/00* (2006.01)
*A61P 11/00* (2006.01)
*A61L 2/10* (2006.01)
*A61L 2/08* (2006.01)

(52) U.S. Cl.
CPC ............... *A61N 2005/1061* (2013.01); *A61N 2005/1091* (2013.01); *A61N 2005/1098* (2013.01)

(56) References Cited

U.S. PATENT DOCUMENTS

| | | | |
|---|---|---|---|
| 2005/0080466 A1* | 4/2005 | Homer | A61N 5/0616 607/88 |
| 2014/0107496 A1* | 4/2014 | Hellstrom | A61B 1/05 600/478 |
| 2015/0117601 A1* | 4/2015 | Keeve | A61B 6/5241 378/41 |

* cited by examiner

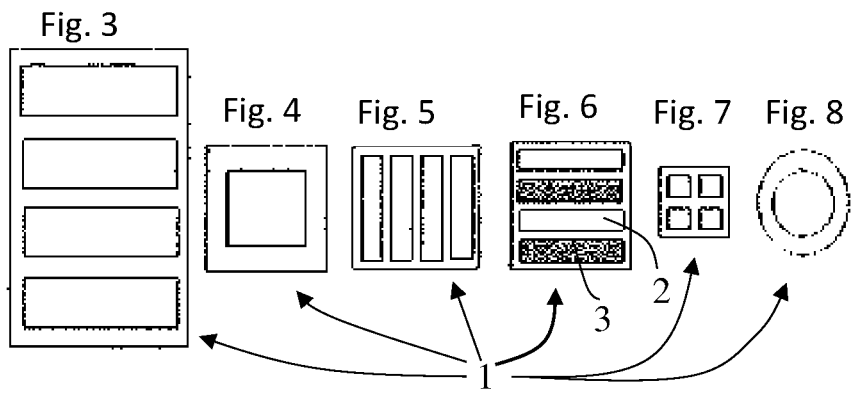
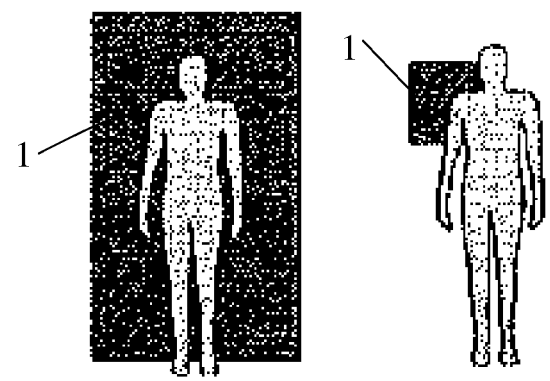
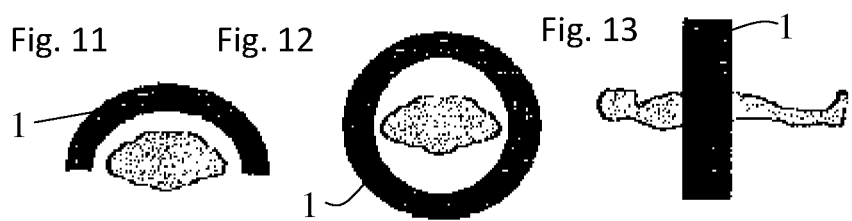

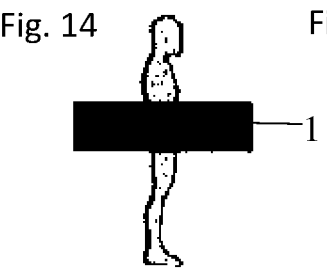
Fig. 14  Fig. 15
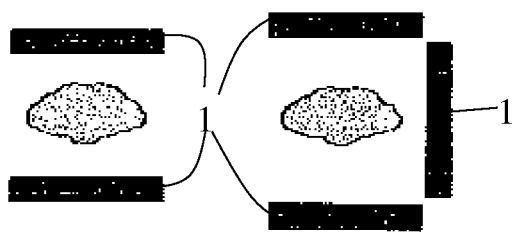
Fig. 16  Fig. 17  Fig. 18
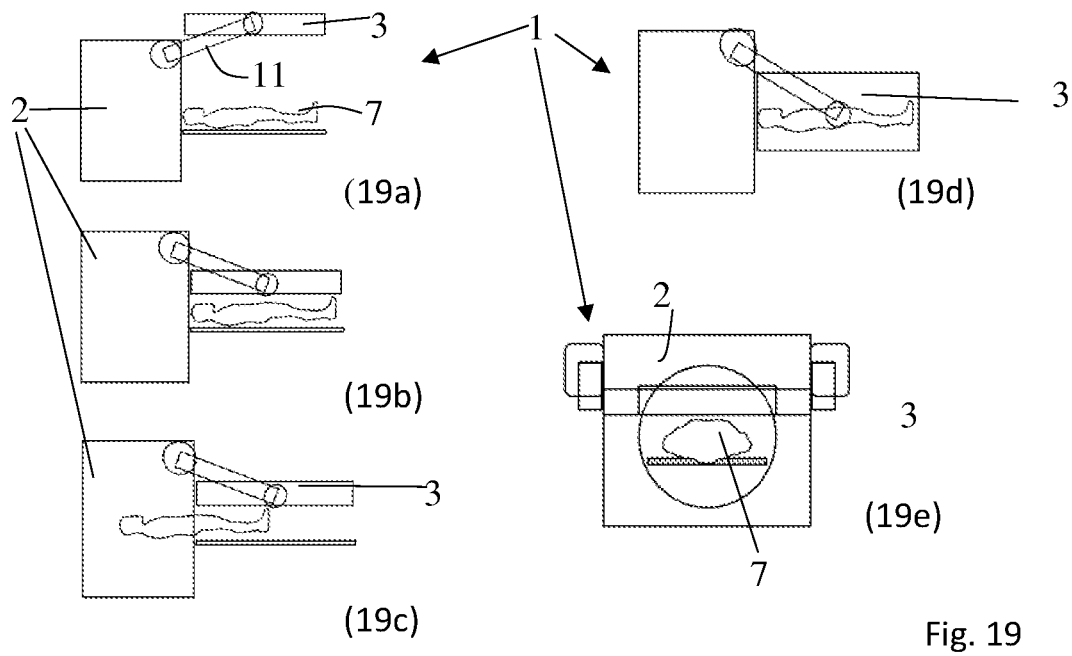
Fig. 19

APPARATUS FOR USE IN IRRADIATION THERAPY COMPRISING IONIZATION MODULE AND UV-LIGHT SOURCE

FIELD OF THE INVENTION

The present invention relates to an apparatus for use in irradiation therapy, comprising an ionization module adapted to emit ionization irradiation and a ultraviolet light source to emit UV-irradiation, and a power source and a control unit to provide a user interface. The invention also relates to a use of the apparatus for irradiating an object and use of the irradiation method in the treatment of a mammal.

BACKGROUND OF THE INVENTION

The ultraviolet radiation or ultraviolet light is an electromagnetic radiation whose spectrum range between wavelengths from 400 nm down to 100 nm, i.e. 750 THz to 30 PHZ. The minimum wavelength which can be seen by healthy people is 310 nm. The wavelengths of the ultraviolet spectrum is shorter than that of visible light which is considered to range from 770 nm down to 390 nm. At wavelengths shorter than the ultraviolet spectrum X-rays begin.

The ultraviolet spectrum is divided into three wavebands, Ultraviolet Type A, Type B and Type C. Ultraviolet A (UVA) ranges from 400 nm down to 315 nm, ultraviolet type B (UVB) range from 315 nm down to 280 nm and ultraviolet light type C (UVC) range from 280 nm down to 100 nm.

While UVC is absorbed in the ozone layer lies 5% of the sunlight that reaches the earth within the UVA and UBVs spectra, and 98.5% of it, is within the UVA waveband. An overview of the different light sources for ultraviolet light and their effects can be found in (Heering, W. 2004)).

Electromagnetic irradiation of the ultraviolet spectrum, ultraviolet light type A (UVA) or ultraviolet light type B (UVB) is used for the treatment of various skin disorders without any photosensitizer is administered and is then called phototherapy. When phototherapy is used together with a photosensitizer for treating skin diseases it is called photochemotherapy. Electromagnetic irradiation from the visible spectrum can be used in blue light therapy for neonatal jaundice or in photodynamic therapy. Monochromatic light in different forms is used in different forms of laser.

In India phototherapy and photochemotherapy was used in year 1400 BC in the treatment of vitiligo (Srinivas Pai C. R. and S. 1997). Psoralen is still used along with sunlight where the patient is administered psoralen and subsequently exposes themselves to sunlight for a predetermined time. When Niels Finsen received the Nobel Prize in 1895 for the treatment of tuberculosis, the first modern era of phototherapy began. A new breakthrough came close to a hundred years later in 1974 when Parrish reported the usefulness of UVA lamps with high intensity (Parrish J. A. et al. 1974). Photochemotherapy with psoralen and UVA (PUVA) thereafter began to be used in large populations in vitiligo and psoriasis. Four years thereafter introduced Wiskeman broadband UVB in 1978 for the treatment of psoriasis and uremic pruritus (Wiskeman A. 1978).

The side effects within the UV-technology was reduced when monochromatic studies showed that the spectra effective against psoriasis was different from the spectra that caused the erythema evoked by UV-light (UV-erythema) (Parrish, J. A., K. F. Jaenicke 1981)

Technically this is solved while the spectra of a particular lamp can be modified with different phosphor coatings on the inside of the lamp. Fisher et al showed that a narrow band at 313 nm is particularly effective against psoriasis with a reduced effect on flushing. Thereafter the fluorescent light (Philips TL-01) containing phosphorus which produced a peak with a narrow band with an emission at 311±2 nm and a minor peak at 305 nm was developed.

Commercially viable narrowband UVB lamps (NBUVB) came 1988.

Long-wave UVA has a wavelength between 340-400 nm and filters out wavelengths that gives the redness from UVA and UVB (290-340 nm).

Ultraviolet light may interfere with the cell cycle and the cell division. UVA penetrates deeper and has effects in the epidermis and dermis, while UVB which reaches mainly the epidermis has stronger effects where NBUVB for example induces apoptosis of the Langerhans cells in the epidermis. Photochemotherapy with psoralen and UVA (PUVA) has a number of effects on the cells and the effects of repeated therapy can also be seen on the cytokines produced by the cells (Stern R. S. 2007)

Phototherapy devices are of different sizes and can be used in hospitals, or at home.

Phototherapy and photochemotherapy use various types of light sources and within photochemotherapy there is many ways to apply the photosensitizing substance like I. Natural sunlight, Dead Sea therapy and photochemotherapy with the sun "PUVA sun"

II. Artificial light sources including; UVA alone, BB-UVB, NB-UVB

III. Sensitized phototherapy; systemically given PUVA (Oral psoralen+UVA); Topically applied PUVA (Topical psoralen+UVA); bath PUVA Psoralens are naturally occurring tricyclic furanocoumarins. All citrus contain psoralen. Plants that contain furanocoumarins are listed (Pathak M. A. 1951).

Natural psoralens are 8-Methoxypsoralen (8-MOP) and 5-Methoxypsoralen (5-MOP), the synthetic analogues are less phototoxic orally, but more phototoxic upon application.

UVA can itself alter DNA by a type-1 oxidative mechanism at the 5'-G of 5'-GG-3' linkage of double stranded DNA and may photosensitize a range of compounds to reactions with DNA (Hiraku Y. 2007). UVA may if furanocoumarins are intracellular when the UVA hits the cell, create bonds between the furanocoumarins and the DNA strands via a photochemical reaction between the furanocoumarins and the pyrimidines of DNA (Barry S. 1976). These chains can be repaired through breakage of the chains. An overview of the bonds between the different types of furanocoumarins and the DNA is provided in Barry S. 1976. The bonds may be repaired by a living cell if they are few, but when they are too many, the cell enters programmed cell death i.e. apoptosis, or if the cell is far too damaged it enters necrosis.

Another overview of the various bindings and a method "Comet repair" that is used to detect them is disclosed in Wu J. et al. 2009.

PUVA is an established therapy for about twenty skin diseases. For details on various PUVA protocols (see Srinivas C. R. and Pai S. 1997). PUVA induces a variety of immune reactions and what mediates the actual suppression of the immune system is not clearly defined, but one of the effects considered is that it reduces the number of immune cells in the skin. PUVA changes the phenotype, e.g. the surface structures on cells and induces apoptosis in the cells of the skin, including cells of the immune system, such as T cells and antigen presenting dendritic cells (Stern, R. S.

2007). PUVA has also been proven to reduce the type 4 immune reactions (Wolf et al. 2016). In animal models that have been administered PUVA, cells with immunosuppressive effect has been isolated from organs beyond the skin, such as the lymph nodes and spleen. These cells have been able to reduce antigen-specific type 4 reactions in the skin both in the animal that has received PUVA therapy, but also from syngeneic animal models (Wolf et al. 2016).

PUVA can also be provided outside the body, directly on the cells in the blood, which then are returned to the patient (extracorporeal PUVA). Ultraviolet light together with psoralen and other photosensitizing substances are also used to sterilize blood products or disabling the immune cells in blood products before transfusion (Cardo C. et al., 2007, Seghatchian 2012). UVC alone is also used in this area and for the disinfection and purification of water from among other things pharmaceutical products (Pour Akbar M. et al. 2016).

If the skin of an animal or a human is the first area that is hit by UVB, the UVB affects mainly cells in the epidermis, while UVA affects cells in the epidermis and dermis. If a thin layer of fluid or plasma is illuminated, both UVA and UVB pass the cells in the liquid with good effect. Ionizing irradiation is used therapeutically e.g. to create medical images in radiology but also in oncology as irradiation therapy. Artificially UVC, which is ionizing and normally disappears in the Earth's ozone-layer, is used to sterilize surfaces.

Ionizing irradiation is irradiation that can ionize atoms by exciting electrons in the atoms' electron shells enough for them to leave the atoms. An atom, where an electron has left, or an atom in which an electron is added to the electron, shell forms an ion.

Ionizing irradiation can be divided into sub-atomic particles that move at high speed and into electromagnetic waves. The sub-atomic particles can be alpha-particles which are helium nuclei (4He). When they are created by the radioactive decay, they can be stopped by a sheet of paper, or by the skin.

Beta particles consists of electrons or positrons, which can be stopped by a sheet of aluminium. Beta particles can be detected by the Geiger counter. Beta particles can create X-rays (Bremsstrahlung) especially, when they are slowed down by a material with high atomic number. Beta particles can also create delta rays (secondary electrons as they pass through materials).

Photon irradiation is called gamma irradiation, if it is produced by a reaction involving the atomic nucleus, such as nuclear reactions, subatomic particle decay or radioactive decay within the atomic nucleus. If the photon is created outside the nucleus, it can give rise to X-rays. X-rays is conventionally defined as a wavelength of 10-11 nm or a photon energy of 100 keV. A classic X-ray tube creates photons with an energy below 100 keV, which are absorbed through the photoelectric absorption of organic materials. At energies beyond 100 keV, photons ionize matter through the Compton effect and then indirectly through the production of pairs of energies beyond 5 MeV.

Gamma irradiation consists of photons with high energy, which may be absorbed when crossing dense materials. Neutron (n) irradiation consists of free neutrons, which are blocked by light elements, such as hydrogen, which can slow down and catch them. Cosmic irradiation consists of charged nuclei, such as protons, helium nuclei, and nuclei with high charge, known as "HZE ions". When the particles in the cosmic radiation is entering the atmosphere they are stopped by the molecules in the air thus creating short-lived pions that are broken down into muons, which is the type of cosmic irradiation that reaches and partly penetrates into the soil surface.

Within radiology, mainly X-ray are used for a variety of types of imaging examinations. All X-ray examinations carry a risk of DNA-damage, which, within the investigated population, increases the risk for cancer. Since the introduction of the technology, radiology, and in recent years the computer tomography's has developed and the irradiation doses has been reduced.

Irradiation therapy was first used after the discovery of X-rays in 1895 and uses electromagnetic irradiation within the X-ray and gamma spectrum to treat cancer.

Irradiation or irradiation therapy works by damaging DNA. When cancer cell DNA is damaged, their ability to proliferate decrease. DNA can be damaged by two types of energy, by the action of photons (electromagnetic irradiation) or by the action of charged particles. Electromagnetic ionization irradiation within the X-ray and the gamma area is called phototherapy and provides a higher proportion of single stranded DNA damage compared to the particle irradiation, which gives a higher percentage of double-stranded DNA damage. The damage is directly or indirectly ionizing the atoms which create the DNA chain. Indirect ionization happens by ionization of water or oxygen, creating free radicals. The free radicals then damage the DNA. In photon therapy, most of the irradiation effect comes from free radicals. Charged particles, such as protons and ions of e.g. carbon and neon, damage DNA through direct energy transfer which creates double-stranded DNA damage. Any repair of DNA-damage is time dependent, and if the cell received a irradiation dose that it is able to repair, the number of DNA damages are reduced over the time after the irradiation treatment. Various types of enzymes are involved in various types of DNA-repair. Cancer cells from some types of tumours have a reduced ability to repair DNA-damage. Some cancer cells that divide rapidly are susceptible to damage on one DNA strand then passed on to the next generation. Some types of activated immune cells are on the other hand repairing DNA damage faster than cells that are dormant when irradiation strikes them. "Nucleotide excision repair" (NER) and "base excision repair '(BER) repair cells most quickly. When it comes to damage that wholly or partially broke the DNA-strand, the body most easily repairs "single-strand-breakage" (SSB) on the DNA-molecule, while the "double-strand-breakage" (DSB) will take longer to repair. Cells can normally repair minor damage on DNA by ionization irradiation equivalent to an X-ray examination, while higher doses of ionization irradiation can overload the cell's repair capacity and be fatal. By irradiation that does not kill the cell, the number of DNA-damage is the highest right after the energy has been transferred to the DNA while the DNA-damage subsequently starts to be repaired (Nocentini S. 1999 Banath P. 1998).

Irradiation therapy is used by different protocols to maximize the damage to cancer cells and to minimize the secondary damage to the surrounding tissue. In order to achieve maximal damage to the cancer cells and less damage to the surrounding tissue fractionated irradiation therapy is applied. Irradiation therapy is associated with damage directly on cell function. This may have the adverse effect of hair loss, which may occur at 1 Gy. There is also a risk that DNA-damage causes mutations, which in turn can lead to cancer. Overall, it is very important to hold the irradiation dose down to prevent side effects.

Radio nucleoid therapy is developed to reduce adverse effects of irradiation therapy (Kumar C. 2016)

Regarding systemic action, as referred to phototherapy and photochemotherapy effect on type-4 reactions in the skin, decreases in humans after repeated treatment with UVB and PUVA. Regarding systemic action on for example psoriasis, which is also a skin disease, phototherapy is compared to UVB and photochemotherapy with UVA with cyclosporine. Sometime photochemotherapy (PUVA) works in cases where phototherapy (UVB) does not work. The perception is that photochemotherapy acts locally for skin diseases, such as psoriasis, by induced cell death and local immunosuppression. The part of the inhibition of the immune system that has been shown to affect parts of the skin surface not irradiated with photochemotherapy The prevailing view is that the irradiation treatment prevents phototherapy or photochemotherapy because radiotherapy affects the cells of the skin, which then phototherapy or photochemoterapy in turn will affect. Any effect on diseases of internal organs has not been demonstrated and the view from leading researchers within the medical field is that ionization irradiation should reduce the possibility of a systemic effect of UVA or UVB because ionization irradiation also reduces the number of T cells and dendritic cells in the skin, which phototherapy and photochemotherapy should operate on. It is, inter alia, the DNA-damage in these cells that can lead to apoptosis and immunosuppression, which is called systemic, when it can be detected in a type-4 reaction in response on a different part of the skin surface.

DNA-damage in prokaryotic and eukaryotic cells can occur after contact between nucleotides and pharmacologically active substances with or without concomitant ultraviolet light e.g. psoralen, 4,5',8,-trimethylpsoralen, 8-Methoxypsoralen, angelicin, 3-carbethoxypsoralen, Cis-diaminedichloro pt (II) (cis-DDP), trans diamminecihloro pt (II) (trans-DDP), Nitrogen mustard, "half"-nitrogen mustard, cyclophosphamide and nitrosourea.

The repair rate of the DNA-damage is increased in activated immune cells and substances such as serotonin inhibitors can increase the rate of repair of DNA damage (Wolf P. 2016)

Both UVA and ionization irradiation is used for different areas within medicine, bio technique and technique, but apparatus for simultaneous or concomitant administration of the forms of irradiation on materia or living cells do not exist.

U.S. Pat. No. 5,317,574 discloses an apparatus that allows focus of a irradiation wavelength within a small bandwidth. The apparatus is used for emitting irradiation at a wavelength below 100 nm. The apparatus is adapted to either use X-ray or UV irradiation

OBJECT AND SUMMARY OF THE INVENTION

It is an object of the present invention to at least partly overcome the above problems, and to provide an improved apparatus for use in irradiation therapy that may administer ultraviolet light and ionization irradiation, in one or several combined or alternately pulsations.

This object is achieved by the apparatus as defined in claim 1.

The apparatus comprises
an ionization module adapted to emit ionization irradiation, and
a power source and a control unit to provide a user interface.

The apparatus is characterized in that the apparatus comprises an UV module adapted to emit UVA, UVB and/or UVC irradiation, whereby the ionization module and the UV module emit irradiation simultaneously or alternately, and the ionization module emits irradiation at a wave length at least below 100 nm.

The apparatus of the invention is believed to create a synergy to induce DNA-damage. including photochemical DNA-damage in living cells. The synergy between one or more combined or alternately irradiations during a treatment may give an increased effect e.g. more DNA-damage per consumed time and energy. It is anticipated that the apparatus may give less side-effects and a more effective and efficient treatment than existing apparatus for irradiation, radiology and phototherapy. This is believed to be due to precise preprogramed combined and alternately irradiations of ultraviolet light and ionization irradiation as delivered by a combined apparatus. It is believed that the apparatus may turn the immunological effect of the DNA-damage caused by frequent imaging radiology in a human to a therapeutic use by adding a tailored amount of DNA-damage caused secondary to ultraviolet light, with or without photochemistry. In specific is believed that the apparatus may turn the immunological effect of the DNA-damage caused by frequent imaging radiology in a human to a therapeutic use by adding a tailored amount of DNA-damage caused by photochemotherapy.

In one embodiment, the irradiation is emitted simultaneously and sequentially.

In another embodiment, the ionization module comprises an anode, a cathode opposite the anode and a detector.

In a further embodiment, the UV module comprises a light source adapted to emit light at a wave length between 100 and 450 nm.

In one embodiment, the ionization irradiation is photo irradiation or particle irradiation.

In another embodiment, the ionization irradiation is X-ray or gamma-irradiation at a wave length between 0.001 and 10 nm.

In a further embodiment, the ionization irradiation is X-ray.

In a further embodiment, the UV irradiation is UVA and/or UVB irradiation at a wave length between 280 and 400 nm.

In one embodiment, the UV irradiation is UVA irradiation at a wave length between 315 and 400 nm.

In another embodiment, the UV irradiation is UVB irradiation at a wave length between 280 and 315 nm.

In a further embodiment, the UV irradiation is UVC irradiation at a wave length between 100 and 280 nm.

The invention also relates to a method for radiating an object, comprising
providing an apparatus comprising
an ionization module adapted to emit ionization irradiation,
an UV module adapted to emit UVA, UVB and/or UVC irradiation,
a power source and a control unit to provide a user interface,
emitting irradiation from the ionization module and the UV module simultaneously or alternately, for a period of time, whereby the ionization module emits irradiation at a wave length at least below 100 nm.

The apparatus achieves a maximal effect on DNA with a minimal dose of irradiation. The effect may be directed against an object of dead material or living organisms. The goal may be disinfection of water or other liquid or a degradation and purification of products from microorganisms. The product may be pro- or eukaryote cells, blood products as for example plasma or platelets, an animal, or a part of the body of an animal, a human or a part of the body of a human.

The apparatus allows the use of a method of irradiation doses are minimized, both for UV irradiation and ionization irradiation.

The invention relates to a method for use of the apparatus as defined above, comprising
  providing the apparatus as defined above,
  positioning an object to be radiated on a surface, in the proximity of the modules,
  emitting irradiation from both modules simultaneously or alternately for a period of time between 1 minute and 48 hours,
  optionally repeat the emitting irradiation,
  optionally administering one or more photochemically active compounds to the object before or between irradiations. The photochemical compound may be administered as long before the irradiation as the photochemical compound has an effect on the cells that are irradiated. The photochemical compound can be sprayed on the object, topically applied by hand or by a tool, it may be administered per orally, intravenously, intraperitoneally, nasally, intraoculary, intracranally, intracerebrally, intranervously or intratumorally. In the case of per oral administration of 8-methoxypsoralen, an administration 2-4 hours before irradiation is optimal. In specific, the apparatus can be used to create a combination between the effects of ionizing irradiation and photochemotherapy.

The surface on which the object is positioned may be a surface of a detector.

The method for using the apparatus is believed to have a synergistic effect for inducing DNA-damage in living cells. This may force these cells into apoptosis or necrosis. The synergy between one or more combined or mixed pulsations of ultraviolet light irradiation and ionization irradiation during a treatment gives an increased effect, e.g. more DNA-damage per unit of time per unit of energy emitted. The precise programmed combined or alternating pulsations of ultraviolet light and ionization irradiation may be delivered by the apparatus of the invention. The new method may have less side effects and a more effective and efficient treatment compared to existing devices and therapies Combining the new method with phototherapy- or photochemotherapy gives the possibility to induce apoptosis in cells. This thus further improves efficiency and effectiveness of the method. One advantageous of the apparatus is to use it to potentiate photochemical energy, where a photosensitizing compound/psoralen has been administered to the object prior to emitting UV irradiation and the ionization irradiation to the object.

In one embodiment of the method, the irradiation is simultaneously and sequentially.

In another embodiment of the method, the period of time for simultaneous irradiation is between 1 and 10 minutes and a non-irradiation period between sequential irradiations is between 5 minutes and 48 hours.

In a further embodiment of the method, the period of time for alternately irradiation is between 1 and 5 minutes for ionization irradiation and between 1 and 10 minutes for UV irradiation with a non-radiating period of between 5 minutes and 48 hours.

The effect of the irradiation treatment impacts the patient's cells by damaging DNA. This damage is at least partly repaired after the irradiation treatment. The ability to repair damaged DNA becomes more difficult the more damage incurs on the DNA. Thus by simultaneous and/or alternating and or sequential treatment of both UV irradiation and ionization irradiation, the irradiation effect on the cells is maximized to an extend that may prevent the cells ability to repair damaged DNA. As a consequence the radiated cells will die.

The process of cell death may be through apoptosis or necrosis.

The invention also relates to use of the apparatus as defined above, or the method of use as defined above, in irradiation treatment of a mammal.

In one embodiment, the treatment is an irradiation treatment of a disease.

In another embodiment, the treatment is an irradiation treatment of cancer.

In an embodiment, the treatment is an irradiation treatment of Acute-Respiratory-Distress-Syndrome.

In an further embodiment, the treatment is an irradiation treatment of pancreatitis In another embodiment, the treatment is an irradiation treatment of multiple sclerosis In another embodiment, the treatment is an irradiation treatment of Graft-versus-host disease (GVHD).

In another embodiment, the treatment is an irradiation treatment of psoriasis

In another embodiment, the treatment is of a steroid resistant e.g. a glucocorticoid resistant disease.

In another embodiment, the treatment is made to decrease the number of th17 cells.

In another embodiment the treatment is made to increase the number of regulatory T-cells or myeloid suppressor cells.

In another embodiment the treatment is made to increase the number of antigen specific cells with suppressive action.

In another embodiment the treatment is made to decrease a delayed-type-hypersensitivity reaction.

In a further embodiment, the treatment is an irradiation treatment for sterilization of an object.

In an embodiment, the object is a surface, a liquid or blood.

The new apparatus gives new possibilities for the treatment of surfaces for disinfection and treatment of blood-products.

The apparatus may give new biochemical, chemical and physical effects within treatment of surfaces and thin materials within areas as varnishing, production of membranes and optics.

BRIEF DESCRIPTION OF THE DRAWINGS

The invention will now be explained more closely by the description of different embodiments of the invention and with reference to the appended figures.

FIGS. 3 to 8 shows different embodiments of the apparatus of the invention in different sizes and shapes.

FIG. 9 illustrates how the apparatus can be used for irradiation treatment of a body of a human.

FIG. 10 illustrates how the apparatus can be used for irradiation treatment of part of a body of a human FIGS. 11 to 13 illustrate different embodiments of the apparatus of the invention in different sizes and shapes for treatment of a horizontal positioned object.

FIGS. 14 to 18 illustrate different embodiments of an apparatus of the invention in different sizes and shapes for treatment of a vertically positioned object.

FIG. 19a-e show how the apparatus can be used for irradiation treatment.

DETAILED DESCRIPTION OF PREFERRED EMBODIMENTS OF THE INVENTION

Following detailed description of the invention, and the examples are provided to describe and illustrate certain embodiments of the invention and do not limit the scope of the invention in any way.

Figure 1:
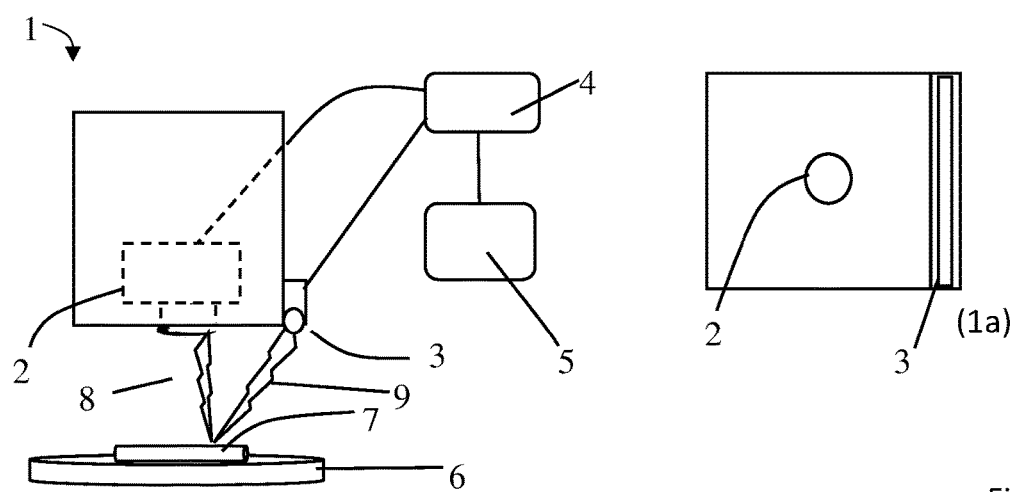
FIG. 1 shows one embodiment of an apparatus of the invention, whereby both irradiation modules in positioned next to each other.

FIG. 1 shows an example of an apparatus 1 for use in irradiation therapy according to the invention.

Figure 2:
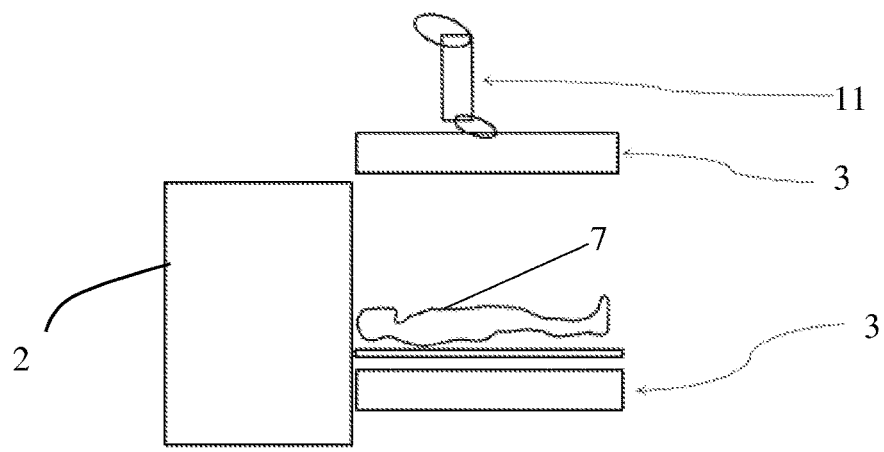
FIG. 2 shows another embodiment of an apparatus of the invention whereby the two irradiation modules are positioned parallel to each other.

The apparatus comprises an ionization module 2, an UV module 3, a power source 4 and a control unit 5. The control unit may provide a user interface with input means, such as a keyboard, and a screen. In one embodiment, more than one power source and/or more than one control unit 5 is used in the apparatus 1. In FIG. 1, both modules are positioned next to each other. FIG. 1a shows a bottom view of the apparatus. FIG. 2 shows another embodiment, whereby the two modules are positioned next to each other, with a computer tomograph (CT) as ionization module and a UV module, held in place by an adjustable member 11, such as an drop arm as shown in FIG. 2. The invention is not limited to these examples and many variations are possible, whereby the two modules are aligned to cooperate for administrating irradiation to an object. In one embodiment, the irradiation may come from the table were the patient is conveyed in supine- or prone position into the CT. Further examples are outlined below.

The ionization module is adapted to emit ionization irradiation 8. This ionization irradiation may be selected from the group comprising or consisting photo irradiation, particle irradiation, X-ray irradiation or gamma irradiation. The wavelength of the ionization irradiation is between 0.0001 and 100 nm, or between 0.001 and 100 nm. The wavelength of X-ray or gamma irradiation may be between 0.0001 and 15 nm, or between 0.001 and 10 nm.

There is a range of different sources of ionization irradiation, both from different sources of ionization irradiation, gamma irradiation and particle irradiation. The ionization module may be an X-ray device or a computed tomograph (CT).

Any X-ray device can be used in the apparatus of the invention. Usually these devices include an anode, a cathode opposite the anode and a detector 6. The object 7 to be radiated is position such that both modules can radiate the object.

The UV module is adapted to emit ultraviolet light (UV) 9 and comprises a light source that can emit light at a wavelength between 90 and 450 nm, or between 100 and 400 nm. The light source may emit light in the UVA range between 315 and 400 nm, or in the UVB range between 280 and 315 nm or in the UVC range between 100 and 280 nm, or any combinations thereof. The light source may be a source having a narrow bandwidth within the UV range (A, B or C) of about 50, or 25 or 10 or 5 or 3 nm.

There is a range of different sources of ultraviolet light type A or type B on the market which are used within medical technique.

The invention concerns an apparatus emits UV and ionization irradiation simultaneously, alternately and/or sequentially in order to administer ultraviolet light and ionization irradiation to an object, in one or several combined or alternately pulsations.

The control unit 5 may include a regulatory system configured to emit the ionization irradiation in one or several pulses before, during or after emitting the UV irradiation. The apparatus may also be configured such that UV irradiation is emitted in one or several periods before under or after the emitting pulses from the ionization irradiation.

One example may be to assemble an UV-lamp together with a X-ray-tube, whereby the emission of UV and ionization irradiation is regulated by the control unit, which "turn on" and "turn off" the UV lamp and the irradiation of the X-ray-tube.

Another example can be a UVB source assembled together with a projector for gamma irradiation, whereby the emission of irradiation is controlled as exemplified above.

A third example can be a UVA and a UVB source assembled together with a source for X-ray irradiation. A fourth example can be a source for UVA assembled together with a projector for gamma irradiation. In the same manner, UVA and/or UVB sources may be assembled together with projectors for particle irradiation.

Alternatively, the UVA and/or the UVB modules may be moved in a lumen of a vessel or an intestine or another cavity of a body and the module/source for ionization irradiation may be outside the body. The position of UVA and/or the UVB module may need to be verified with optics or by radiography. This allows for very precise targeting of an object inside a body, thereby minimizing side effects of irradiation.

The sources for ultraviolet irradiation and ionization irradiation may be placed mixed in a grid, the sources of light or the sources of ionization irradiation may be square sized or circular or of any other polygonal shape or form. The number of sources of UV-light or ionization irradiation may depend on the size of the apparatus.

The sources of ultraviolet light and ionization irradiation may be positioned in a way so that the modules envelope each another mixed linearly, the sources of light or the sources of ionization irradiation may be square or circular or of any polygonal shape. The number of sources of UV-light or ionization irradiation may vary dependent on the size of the apparatus.

FIGS. 3 to 8 show the apparatus in different sizes and forms. The UV module and the ionization module may be positioned differently with regards to each other. These are only illustrative and the number of areas within each apparatus may be more or less than what is shown in these figures. The different examples on positioning and the different size and shapes of the modules need to be coordinated with each other.

FIGS. 9 and 10 show how the object can be placed in relation to the apparatus. As shown in FIG. 6, the UV module and the ionization module may be positioned in alternating rows.

Alternatively, as shown in FIGS. 5 and 7 one module may fill the circumference of the other module. FIG. 8 shows the apparatus in the form of a circle that can circumvent the object.

FIG. 9 shows how the apparatus can be used for irradiation of a body of an object, such as a human. 10. The apparatus can cover the total area of the object and even enable to allow an even irradiation of the total object area. The apparatus may be assembled to circulate around the object, or the object may circulate inside the apparatus.

FIG. 10 shows how the apparatus can be used for irradiation of part of a body of the object.

A smaller size of the apparatus can be used when the object is in standing position. The modules may be positioned in turn or with one module circumventing the module or any other variation thereof. These smaller forms of UVII may be developed to cover a part of a human, and may be able to move back and forth, up and down or around a patient. The smaller apparatus may also be shaped in a size that is suitable for irradiation of a film or fluid, or a bag with fluid, a surface or an item that passes on a transporter.

The modules may be removably mounted on a grid. The modules may also be removably mounted on a tripod or stand or frame. Such stands may be of different types dependent on the object to be radiated and the environment where the apparatus is to be used. The design of the stand is also dependent on what type of ionization irradiation that is to be combined with ultraviolet irradiation, where different forms of ionization irradiation may suit better than others to be emitted from a certain kind of source. If the module is small in relation to the object the object instead has to be moved back and forth under the module, or the module has to be moved back and forth over their object until the intended treatment effect has been reached.

The stand that the apparatus is assembled on may be portable. The apparatus may be conformed in a way that it is placed within a shield that is easy to disinfect by e.g. 5% chlorhexidine or 70% alcohol or another suitable solution for disinfection such that apparatus easily may be moved between different objects or patients without the risk for contamination within or between places on sites, such as hospitals. One part of or the entire shield may be transparent to allow passage of irradiation.

The apparatus may be assembled on a vehicle or on a drone or on a remote vehicle or a robot, including a vehicle with a pre-programmed movement pattern.

The apparatus may be part of a line of production where the apparatus is radiating towards a conveyor.

The apparatus may fastened on a therapeutic instrument that is introduced endoscopically into a vessel, into the peritoneal cavity, gastro- or colposcopy- or through the urinary tract retroscopically or antegradely likewise through the choledoccus.

In FIG. 11 the apparatus has a semi-circular form, and in FIG. 13 the apparatus has a circular form. FIG. 12 shows a cross section of the apparatus in FIG. 13 showing the object inside the circular apparatus. The apparatus may have an elliptic form. The apparatus that radiates only one part of the object. In these cases, the apparatus may move over the part of the object to reach a larger part of the object, or the object may move below the apparatus.

FIG. 14 shows the apparatus having a circular form and FIG. 15 shows a cross section of the apparatus in FIG. 14 from a top side. FIG. 16 shows a combination of a semi-circular unit and a straight unit.

FIGS. 16 and 17 show other alternatives for positioning the units around the object. The units may comprise one module each or the units may comprise a combination of the UV module and ionization module. In one embodiment, one unit comprises the ionization module and the other unit comprises the UV module. In another embodiment, each unit comprises both modules, whereby the modules are positioned alternately in parallel or one module may be positioned around the other module. The modules are positioned on the inside, which enables the whole object to be radiated concomitantly.

The shape or form of the apparatus can actually be any at all. When the apparatus has an oval-, semi-circular-, three-quarter- or a round shape, it may move back and forth, or up and down or around the object. Likewise the object may move in relation to the apparatus.

The apparatus may also be used to emit irradiation onto everything around, as a circular or a semi-circular apparatus that radiates outward in all directions on the whole or half the room, respectively. In the case where the human may be totally enveloped by the apparatus, the apparatus may be fitted with a door, with the apparatus mounted on the inside, which allows for the whole object or human to be radiated at the same time.

Even if the figures show an adult human body, the apparatus may be fitted in a size and shape for children of different ages as well as for other objects in different sizes and shapes.

It is an advantage if the UV modules and the ionization modules are positioned in a way so that they give an even exposure on the intended object. The spread of the UV irradiation or ionization irradiation ionization determine how the modules may be positioned, both in relation to each other, but also in relation to the distance to the object and the size of the object in width, height and dependent on whether the object itself shifts in depth in relation to the modules.

The maximal effect of the apparatus is accomplished when the irradiation hit different parts of the object. Another alternative is that the object is moved in relation to the apparatus in a way so that different parts of the object are hit with the maximal effect of the apparatus during different parts of the irradiation session.

Another variant may be that the UV-light is given from several directions from a semi-circular or from a polygonal shaped apparatus or UV module, while the ionization irradiation is given from an opposite direction. In the same way, the ionization irradiation is given from several directions, i.e. from a semi-circular or from a polygonal form of the ionization module and the UV-light is given from an opposite direction from the UV module. ionization FIG. 19 illustrates how the apparatus of the invention can be used in a method for radiating an object. The method comprises providing the apparatus as defined above and any variation thereof. A power source 4 and a control unit 5 may be present to provide a user interface. In FIG. 19a, the UV module 3 is positioned above the object or human and the ionization module 2 is positioned behind the object 7. After placing the object or human on the apparatus 1 as shown in FIG. 19b irradiation may be emitted from the UV module. In this embodiment, the object is first moved or placed into the ionization module before emitting ionization irradiation (FIG. 19c). The ionization module may be a computed tomograph (CT), which is a device with an imaging procedure that uses special X-ray equipment to create detailed pictures, or scans, of areas inside the body. Once the object is inside the CT irradiation can be emitted from the ionization module and the UV module simultaneously or alternately, for a period of time (FIG. 19d), whereby the ionization module emits irradiation at a wave length at least below 100 nm. FIG. 19e shows a cross section of the apparatus in FIG. 19d through a vertical axis. The irradiation from the two modules may be emitted simultaneously and sequentially as well.

The period of time for simultaneous irradiation may be between 0.1 and 30 minutes, or between 1 and 10 minutes and a non-irradiation period between sequential irradiations may be between 1 and 7 days, or between 5 minutes and 48 hours.

The period of time for alternately irradiation is between 0.1 and 30 minutes, or between 1 and 5 minutes for ionization irradiation and between 1 and 10 minutes for UV irradiation with a non-radiating period of between 1 and 7 days, or between 5 minutes and 48 hours.

The apparatus may be comprise a UV module that emits only one peak (a small bandwidth of wavelength) of UVA or UVB. Likewise, the ionization module may be adapted to emit one peak of ionization irradiation. For example, there may be only one peak of emission in the UVB area and one in the gamma-area. The strength of the emitted irradiation may be such that the DNA-damage is larger than the background irradiation within 30, or more preferable 10 minutes, or most preferable within less than five minutes of irradiation time.

Figure 20:
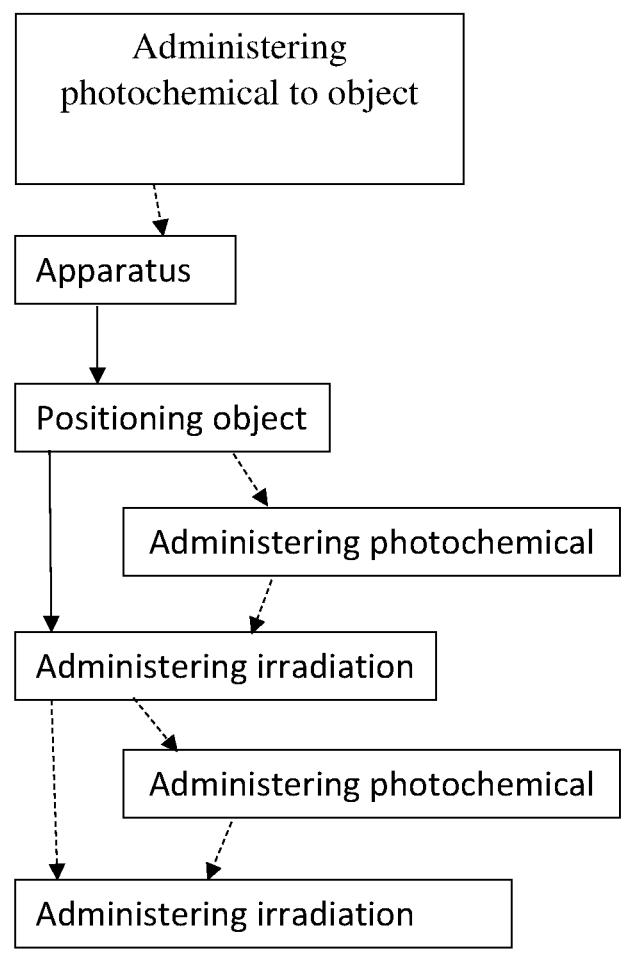
FIG. 20 shows a flow diagram for a method of treating an object using the apparatus.

The invention relates to a method for use of the apparatus as defined above and any variation thereof, for treating an object. FIG. 20 schematically illustrates the method in a flow diagram. The method comprises providing the apparatus as outlined above and positioning an object to be radiated on a surface, which may be a surface of a detector 6. Consequently, irradiation is emitted from both modules simultaneously or alternately for a period of time between 0.1 minute and 7 days, or between 1 minute and 48 hours, Optionally, the step is repeated after a non-irradiation period.

The irradiation from the two modules may be emitted simultaneously and sequentially as well.

The period of time for simultaneous irradiation may be between 0.1 and 30 minutes, or between 1 and 10 minutes and a non-irradiation period between sequential irradiations may be between 1 and 7 days, or between 5 minutes and 48 hours.

The period of time for alternately irradiation is between 0.1 and 30 minutes, or between 1 and 5 minutes for ionization irradiation and between 1 and 10 minutes for UV irradiation with a non-radiating period of between 1 and 7 days, or between 5 minutes and 48 hours.

Photochemically active compounds i.e. psoralens may be used in combination with irradiation therapy. The apparatus can thus be used to provide a photochemical reaction between DNA and one or more psoralen and/or to evoke phytodermatitis, or photosenzibilization in an object to be radiated. One or more photochemically active compound may be administered to the object before or between irradiations.

These photochemically active compounds or psoralens may be selected from the group comprising *Ficus* earica, *Pastinaca sativa, Heracleum sphondylium, Heracleum gigantum*, Pastinaea sativa, Heraeleum mantegazzianum, *Foeniculum vulgare, Anethum graveolens, Peucedanum* oreoselium, *Daucus* earota, Daueus sativa, *Peucedanum ostruthium, Apium graveolens, Ammi majus, Angelica species, Ruta graveolens*, Dictamus albus, *Citrus bergamia, Dictamnus fraxinella, Citrus* aurantiom, *Citrus aurantifolia, Citrus aurantifolia,* var. Swingle, Renuneulus species, Brassiea species, Sinapsis arevensis, *Convolvulus* arevensis, Agrimony eupatoria, Achilleae millefolium, *Chenopodium species, Psoralea* coryiloli, *Hypericum perforatum* or *Hypericum concinnum*, psoralen, xanthotoxin, bergapten, isoimperatorin and bergamotin, or66-97-7, 7H-Furo[3,2-g]chromen-7-one, Ficusin, Furocoumarin, Psoralene, 7H-Furo[3,2-g][1]benzopyran-7-one, Psorline-P, furo[3,2-g]chromen-7-one, Furo[3,2-g]coumarin, 6,7-Furanocoumarin, 7H-Furo[3,2-g]benzopyran-7-one, NSC 404562, Furo(2',3',7,6)coumarin, Furo(4',5',6,7)coumarin, Furo[2',3':7,6]coumarin, Furo[4',5':6,7]coumarin, UNII-KTZ7ZCN2EX, Furo (3,2-g)-coumarin, 7H-Furo(3,2-g)(1)benzopyran-7-one, CCRIS 4343, CHEMBL164660, Furo[2'.3':7.6]coumarin, CHEBI:27616, HSDB 3528, ZCCUUQDIBDJBTK-UHFF-FAOYSA-N, TNP00293, EINECS 200-639-7, BRN 0152784, 6-Hydroxy-5-benzofuranacrylic acid beta-lactone, 5-Benzofuranacrylic acid, 6-hydroxy-, delta-lactone, 2-Propenoic acid, 3-(6-hydroxy-5-benzofuranyl)-, delta-lactone, Manaderm, Psoralene (DCF), Manaderm (TN), Furo[4',7] coumarin, KTZ7ZCN2EX, Oprea1_841692, SCHEMBL17835, MLS001304059, Bio-0831, P8399_SIGMA, furano[3,2-g]chromen-2-one, AC1L1M09, MEGxp0_001172, ACon1_001579, CTK2F4103, pyrano[5,6-f]benzofuran-7-one, 2H-furo[3,2-g]chromen-2-one, MoI-Port-001-741-377, 7-furo[3,2-g][1]benzopyranone, HMS2267L05, ZINC120283, HY-N0053, 7H-Furo[3,2-g]chromen-7-one #, ANW-73223, BDBM50331544, DNC000841, DNC001160, KT6528, MFCD00010520, NSC404562, ZINC00120283, AKOS004110987, AN-8451, CS-3756, MCULE-2236160968, NSC-404562, RTX-010528, NCGC00017351-01, NCGC00017351-02, NCGC00017351-03, NCGC00142529-01, 4CN-1081, AC-20293, AJ-11687, AK105376, BT000248, DR000253, LS-70690, PL066320, SC-18328, SMR000112587, ST057250, ZB004095, KB-249864, FT-0603268, N1332, P2077, ST24045730, W1301, C09305, D08450, P-7850, 6-hydroxy-5-benzofuranacrylic acid delta-lactone, 6-hydroxy-5-benzofuranacrylic acid gamma-lactone, 5-19-04-00445 (Beilstein Handbook Reference), A835599, 3B2-4155, I06-0551, BRD-K47264279-001-01-4, 5-Benzofuranacrylic acid, 6-hydroxy-, .delta.-lactone, 7H-Furo[3,2-g]benzopyran-7-one; Furo[3,2-g]coumarin, 3-(6-Hydroxy-5-benzofuranyl)-2-propenoic Acid|A-Lactone, 3-(6-hydroxy-5-benzofuranyl)-2-propenoic acid delta-lactone, 2-Propenoic acid, 3-(6-hydroxy-5-benzofuranyl)-, .delta.-lactone, and InChI=1/C11H603/c12-11-2-1-7-5-8-3-4-13-9(8)6-10(7)14-11/h1-6.

Most commonly used photochemically active compounds or psoralen are 8-Methoxypsoralen (8-MOP) and 5-Methoxypsoralen (5-MOP).

Irradiation by the apparatus is believes to create synergy between the effect of UV irradiation and ionization irradiation in the DNA of the object. The invention also can be used for disinfection of surfaces, blood products, cell therapies and biotechnical products and may be used in therapeutic purposes in humans and animals. The apparatus may be used together with pharmaceuticals or substances that increases the effect of the UV irradiation or ionization irradiation as mentioned above. One example of such a use is the use of the apparatus together with photosensitizing substances, e.g. furanocoumarins, in a manner that is made in photochemotherapy or in extracorporeal photophoresis or when platelets are treated before transfusion of blood. The invention also may be used together with radio nucleoid therapy.

When it comes to the DNA-damage, induced by UVA combined with photochemotherapy and ionization therapy, such as particle irradiation, within the mentioned periods of time, it is enough if the DNA-damage or the change in DNA, which may be photo chemically induced bindings from furanocoumarins and DNA, only is measurable when it is combined with photosensitizing substances as administration of 8-MOP topically or per orally or with a solution of DNA or living cells or blood before exposures of UVA.

The synergistic biological effects is especially useful for patients that has received total-body-irradiation in combination with bone-marrow-transplantation. Within hundred days after bone-marrow-transplantation the patient may develop an acute graft-versus-host reaction in the skin as well as in one or more visceral organs, such as liver- or gastrointestinal channel. These patients may successfully be treated with photochemotherapy for their graft-versus-host disease of the skin.

In a clinical cohort study of the patients that received total body irradiation before transplantation compared to patients that did not receive total-body-irradiation, it shows that the patients that received total-body-irradiation responded best to photo chemotherapy. Further, patients that received fractionated total-body-irradiation may achieve an increased effect on visceral graft-versus-host disease after photochemotherapy (UVA and 8-methoxypsoralen). The effects of photo chemotherapy is caused by double stranded DNA-damages.

The apparatus used for ionization irradiation and UV irradiation combined with photo chemotherapy concomitantly maximizes the biological effect and minimizes the dose of ionization and UV irradiation.

and the medium (air or liquid) between the object that may absorb the light or ionization irradiation from the apparatus. If the skin is the first area that is hit by UVB irradiation, the epidermis is effecting foremost, while UVA irradiation gives effect in both the epidermis and dermis of the skin. Ionization irradiation may give effect on different depth in the objects' body dependent on the type of ionization irradiation and the setting/protocol of the therapy.

The apparatus may also be used to effect blood, plasma, cells or tissue that may be transplanted allogenically, exogenically or be given back in an autologous manner.

Be used to have an effect on blood or plasma in a circuit that is coupled extra corporeally to a patient. Be used therapeutically, including the used for dermatological diseases as and systemic autoimmune disease as.

One primary effect of irradiation by the apparatus is inducing changes in DNA by an additive or possibly synergistic effect of UV and ionization irradiation. This effect on DNA is even more apparent when irradiation is combined with photosensitizing psoralen. One measure that the effect has been achieved is by measuring the number of single-stranded or double stranded DNA-damages in the living cells that are radiated by the apparatus. Also, the number of regulatory T-cells is expected to be increased in the patient that is treated by the apparatus.

The apparatus may be used in irradiation treatment of a mammal, such as a human. The apparatus may be used on the outer surface or skin of an object, e.g. for the treatment of skin diseases, such as psoriasis, skin cancer.

The apparatus may also be used to treat diseases in the inner organs to treat disease, which affects one or more of the following organs: vessels such as arteries & veins, Table of The conformation of the apparatus in relation to the target of the irradiation of the apparatus (UVII)

| Target: | Round or eleptiform apparatus with irradiation inwards towards the middle | Semi circularly formed apparatus or an apparatus with the form of an ellipse, with irradiation inwards towards the middle | Apparatus formed as a polygon where the irradiation inwards towards the target comes from different directions | Apparatus where the irradiation comes from two opposite directions, e.g. from the front and from behind | Apparatus where the irradiation comes from one direction |
|---|---|---|---|---|---|
| Standing human | The target is a standing human UVII is administered from an apparatus that stretches around | Standing semicircle | Standing in front and at the sides in form of a polygon | Standing in front and behind | Standing in front |
| Laying human | Laying Around | Laying Semicircle | Laying In front and on the sides in form of a polygon | Laying In front or behind (e.g.) on a net or in a hammock of net to let through the light. | Laying In front |
| Part of the body | Part of the body Around | Part of the body Around | Part of the body In front and on the sides in form of a polygon | Part of the body In front or behind (In combination with a net, or the part of the body lays of own weight | Part of the body In front |
| Item | Item Around | Item Semicircle | Item In front and on the sides in form of a polygon | Item in front and behind | Item In front |
| Tube that lets through UVA | Blood tubing | Blood tubing Semicircular | Blood tubing In front and on the sides in form of a polygon | Blood tubing In front and at the sides | Blood tubing in front |
| Fluid film, e.g. Blood or blood product | | Fluid film or thin layer with blood in a semicircle | | | Fluid film, Blood film In front |

The therapeutic effect of the apparatus is dependent on where the apparatus is positioned in relation to the object sinuses, adrenals, parathyroid glands, appendix, thymus, chest, mammae, nipples, pancreas, diaphragm, gall-bladder, brain, hypophysis, joints, liver, uterus, trachea, lip, lungs, stomach, esophagus, spleen, oral cavity, muscles, different sphincter muscles, nerves, kidneys, prostate, skeletal bones, vertebras and cranium, rectum, anus, thyroid, larynx, throat, intestines, testicles, large bowel, duodenum, bladder, veins, ovaries or eyes.

The disease may related to transplantation of organs and may be a rejection after stem cell transplantation, e.g. a graft-versus-host reaction. While the graft-versus-host reaction has similarities to a type-IV-reaction, where activated T-cells attacks antigens, which they are sensitized against, the apparatus could be used against a range of diseases or states following the transplantation.

The disease may selected from the group comprising cancer, including metastasis from the cancer, which involves one or several organs, an autoimmune disease within one or several organs, such as Crohns disease, which may spread to different parts of the bowel or ulcerous colitis, which may engage different parts of the bowel, and also engage liver and gallbladder, an auto-immune disease, which attacks the central nerve system, such as multiple sclerosis, Guillaume Barres Syndrome and Amyotrophic lateral sclerosis, a reaction after a pharmaceutical treatment with a drug that affects the immune-defense, such as the so-called protein therapeutics, which may be recombined cytokine analogues, such as aldesleukin, interking or fusion therapeutics, such as denileukin diftitox, a reaction after a vaccination, an acute-state in the lung, such as acute-respiratory-distress syndrome (ARDS) and chronical inflammation in organs including the lung, such as pneumonitis and fibrosis, acute or chronic inflammations in any organs, e.g. the heart or the kidney.

The apparatus and method can thus be used for the treatment of a mammal, whereby the disease (disorder or illness) may be selected from the group cancer Acute-Respiratory-Distress-Syndrome, pancreatitis, multiple sclerosis and graft-versus-host disease (GVHD).

Because the apparatus administers ionization irradiation, it is necessary that the advantages of the irradiation must be weight against the risks thereof.

The following examples illustrate certain details in the invention and are not intend to limit the scope of the invention in anyway.

An apparatus that administers ultraviolet light or ionization irradiation, in one or several combined or alternately irradiation periods/pulsations.

The ultraviolet light is preferably from the spectra for ultraviolet light of type A and/or type B, i.e. within the spectra from 400 nm to 280 nm, which may include a mix of different emission spectra within this spectra.

It is preferable if the ionisation irradiation which is photon irradiation with wavelengths within the spectra for X-rays and/or gamma irradiation, i.e. within the spectra from 10 nm down to 0.001 nm, which may include a mixture of different emission spectra within this spectra.

It is an advantage if the ionisation irradiation is X-rays. One method where the apparatus is used is to treat material or fluid that has living cells on the surface or within themselves or a combination thereof. One method where the apparatus is used to treat animals or mammals. One method where the apparatus is used to treat humans that has diseases in inner organs. One method is where the apparatus is used to treat humans that has graft-versus-host disease (GVHD). One method where the apparatus is used after administration of psoralen has been provided to the human, the blood product or the surface that the apparatus is illuminating/radiating. It may be preferred if the ultraviolet light is UVA. It may be preferable if the emission-peak in the ultraviolet light in is between 300-400 nanometers. The apparatus may for example be provided with UV module for UVB irradiation and X-rays irradiation, or UVA irradiation and gamma rays irradiation or UVB irradiation and gamma rays irradiation and UVA irradiation and gamma rays irradiation, respectively.

It is a preferable if the UVA is used to induce the photochemical reaction between psoralen and DNA.

The UV irradiation, which is combined with ionisation irradiation may be long-wave UVA and/or narrowband UVB.

Especially, an apparatus that administer UVA and/or UVB and ionisation irradiation of shorter wavelength than UVC is described.

UV irradiation and ionisation irradiation of an intensity that lies above the normal room light, such as ceiling light, point light, indicator lights and lights that are to mark different areas, to administer irradiation in the apparatus for therapy. It is understood that the ionisation irradiation described lies above the background irradiation.

Treatment of an object with the apparatus of the invention is believed to have an effect on systematic disease in human due to the combined effect of ionisation irradiation and photo chemotherapy.

Example 1

Patients with acute graft-versus-host disease in the skin, and in one or both of the visceral organs; (liver or the gastrointestinal channel), that were treated with photochemotherapy for their graft-versus-host disease in the skin were evaluated on whether the visceral graft-versus-host disease was healed or not. 28 patients had been treated with fractionated total-body-irradiation and cyclophosphamide together with the bone-marrow transplantation 35 (13-77) median (min-max) days before start of photochemotherapy. Five patients were not conditioned with total-body-irradiation but instead had received busulfan and cyclophosphamide before the bone-marrow-transplantation. These started photo chemotherapy 26 (13-68) days after bone-marrow-transplantation.

The total healing (complete response) of the visceral graft-versus-host disease was significantly better among the patients who had received total-body-irradiation before photo chemotherapy compared to the patients that had not received total-body-irradiation, (p=0.045).

Example 2

Proof-of-Concept Study on the Effect on Lethal Acute-Respiratory-Distress Syndrome (ARDS) by Tailored DNA-Damage Background ARDS is a common lethal complication secondary to abdominal surgery and pancreatitis.

ARDS has been coupled to an activation of Th17, which also has been identified as a key factor in pancreatitis and pancreatic cancer (Chepalla 2016, Oiva 2010). Apoptosis is an established inducer of tolerance and DNA-damaging pathways are explored to find new drug-targets to induce tolerance (Neves-Costa A and Luis F Moita 2016) Specially, photochemotherapy attenuates Th17 and induces vitamin-D, both which may attenuate ARDS (Furuhashi 2013, Sage 2010, Li Q 2016, Li J T 2005). The combination of low-dose irradiation and photochemotherapy has a synergistic effect in vitro. Separate reports suggest that Low-dose irradiation and photochemotherapy both may affect the CD 4 compartment (Gridley 2009, Singh 2010). The patients with ARDS related secondary to abdominal complications are frequently (every 3-4 day) undergoing computer-tomography (CT)ach a clinical effect by the addition of photochemotherapy within the half-time of repair of double-stranded DNA-lesions from imaging radiology (e.g. CT)<10-30 minutes.
Method After granting an ethical application, to use an animal model of mouse (balb/c) or guinea pig or pig or sheep with intra peritoneal injection of lipopolysaccharide (LPS) with a an LD 50 of 24 h up to one week is used to perform a proof of concept study of a prototype of the combined DNA-damaging method (Gugliemotti 1997, Shi-Ping 2003). Imaging radiology and topical photochemotherapy will be used to induce combined DNA damage.
Outcome Survival of the animal model is evaluated. ARDS is quantified by radiology and NET (Liu S. 2016). DNA-fibre and DNA-comets can quantify the DNA damage. Flow cytometry is used to evaluate the effects on apoptosis (annexin), necrosis (propidium Iodide (PI)), DNA-repair; p53 and p21, and on the lymphocytic cell populations.

Liu S et al. Neutrophil extracellular traps are indirectly triggered by lipopolysaccharide and contribute to lung injury, 2016 Scientific Report November 16. 1-8.

Shi-Ping D. A mouse model of severe pancreatitis induced with caerulein and lipopolysaccharide World J Gastroenterology 2003; 9(3):584-589

Gugliemotti A., Benzydamine protection in a mouse model of endotoxemia, Inflammation res. 46 (1997) 332-335. Zhou M T., Acute Lund Injury and ARDS in acute Pancreatitis: Mechanisms and potential intervention 2010 May 7; 16(17): 2094-2099

Iclozan C., T helper 17 are sufficient but not necessary to induce Acute Graft-versus-host disease Kappel W. IL-17 contributes to CD4-mediated graft-versus-host disease, 2009 Blood, January 22; 113(4): 945-954

Mauermann N., et al. Interferon-gamma regulates idiopathic pneumonia syndrome, a Th17+CD4+ T-cell mediated Graft-versus-host disease. 2008 Pp 379-388, 2008 Chellappa S. et al. Regulatory T cells that co-express ROR-gamma-t and FOXP3 are pro-inflammatory and immunosuppressive and expand in pancreatic cancer 2016, VOL. 5, NO. 4.

Oiva et al. Acute pancreatitis with organ dysfunction associates with abnormal blood lymphocyte signalling: controlled laboratory study 2010, Critical Care 14:R207 Li Q., et al. Resolution of acute respiratory distress syndrome through reversing the imbalance of Treg/Th17 by targeting the cAMP pathway Mol Med Rep. 2016 July; 14(1): 343-8.

Li J T et al. Unexpected Role for Adaptive alpha-beta Th17 Cells in Acute respiratory distress syndrome J Immunol 205 jul 1; 195(1):87-95

Sage R J and Lim H W. UV-based therapy and vitamin D Dermatoll Ther. 2010 January-February 23(1):72-81.

Association between prehospital vitamin D status and incident acute respiratory failure in critically ill patients: a retrospective cohort study BMJ Open respir res. 2015 Jun. 13; 2(1) 1-9 Gridley D. S., et al. International Journal of Radiation Biology 2009, v85:3, pp250-261.

Example 3

Measurements were made with RTI Piranha med dose probe (an external detector) as electrometer. The program used was Ocean, 2014, ver. 2016-12-07. 242.

The source of irradiation was GE C-arm Stenoscop. Soma Technology Inc., the UVA and the X-ray modules tube were mounted in a ninety degree angle in relation to each other (FIG. 1).

Ten seconds measurements of ionization irradiation were done.

| Distance (cm) | UVA irradiation (mW/cm^2) | Ionization irradiation (mGy/s) [min-max] |
|---|---|---|
| 4 | 1.8 [1.7-1.8] | 3.4 [3.4-4.02] |
| 19/32 | 0.9 | 0.92 |
| 32/33 | 0.30 [0.2-0.4] | 0.94 [0.94-1.00] |

The [0.2-0.4] was the difference between the central and the peripheral position of mW/cm$^2$ in the combined target area.

| Vertical position on the tubes | | |
|---|---|---|
| Distance (cm) | UVA irradiation (mW/cm$^2$) | Ionization irradiation (mGy/s) [min-max] |
| 5/10.5 cm | 1.6 [1.6-1.6] | 3.99 [4.00-4.03] |

Example 4

The source for the ionization module is a C-arm Ziehm-Solo and for the UV module a UVA-source.

Measurement of UVA is made on the effect through one-layer of 5mLBD Falcon™ FACS tube on a distance from an object, e.g. a tube to a shield.

Maximum outside shield lateral 0.1, above 0.0 of mW/cm$^2$ in the combined target area.

Measurements were made with pulses of ionization irradiation during one minute.

The detection was made with an electrometer from Solidose and an ionizing chamber from Victoreen m.55-4-5.

| Distance (cm) | UVA irradiation (mW/cm^2) | Ionization irradiation (mGy/s) [min-max] |
|---|---|---|
| 4 | 1.8 [1.8-1.9] | 1.03 [0.67-1.23] |
| 8 | 1.3 [1.0-1.4] | 1.01 [0.89-1.20] |
| 32 | 0.30 | 0.41 |

Example 5

An X-ray tube, Opti 150/30/50HC-100 was assembled together with a Verifix UVA-star 500, 230 V/18 W, length 500 mm. The UV-light was measured with a digital ultraviolet radiometer with a spectral response of 280-400 nm and a peak response of 370 nm, accuracy +−5%, (Bohle, art no BO 55 003 00).

The Verifix UVA star was assembled at a distance where 3.6-3.8 mW/cm$^2$ were administered to the area of the object. The effect drop over the FACS tube plastic was measured to be 50%.

1 mL of fresh buffy-coat blood from human blood donors was aliquoted into 5 ml BD dual snap cap (BD Falcon round-bottom tubes) and a concentration of 1%, 0.1%, 0.05% and 0% of 100% pure Bergamot Eteric Oil from *Citrus Bergamia* peel was added. Then, the tubes were radiated to 0.5 gray with iterated pulses over a 25 minutes period during which the tubes where illuminated with UVA, which was emitted at a dose of 2.76 J/cm² (2.69-2.84).

The ionization irradiation was followed with a run of UVA of 2.76 J/cm² and a run of X-ray 0.5 gray (II).

The cells were held in the dark in a styrofoam box until radiated by the modules, and the non-radiated control cells stayed in the rack in the dark in the styrofoam box during the exposure. After irradiation, all batches were subsequently put into a water bath at 38 degree Celsius for 30 minutes.

The cells where shaken, coloured with trypan-blue and put onto a C-chip of a disposable hemocytometer with Bürker chamber (DHC-B01) for counting the Erythrocytes, Leukocytes, Mammalian Cells, i.e.

Figure 21:
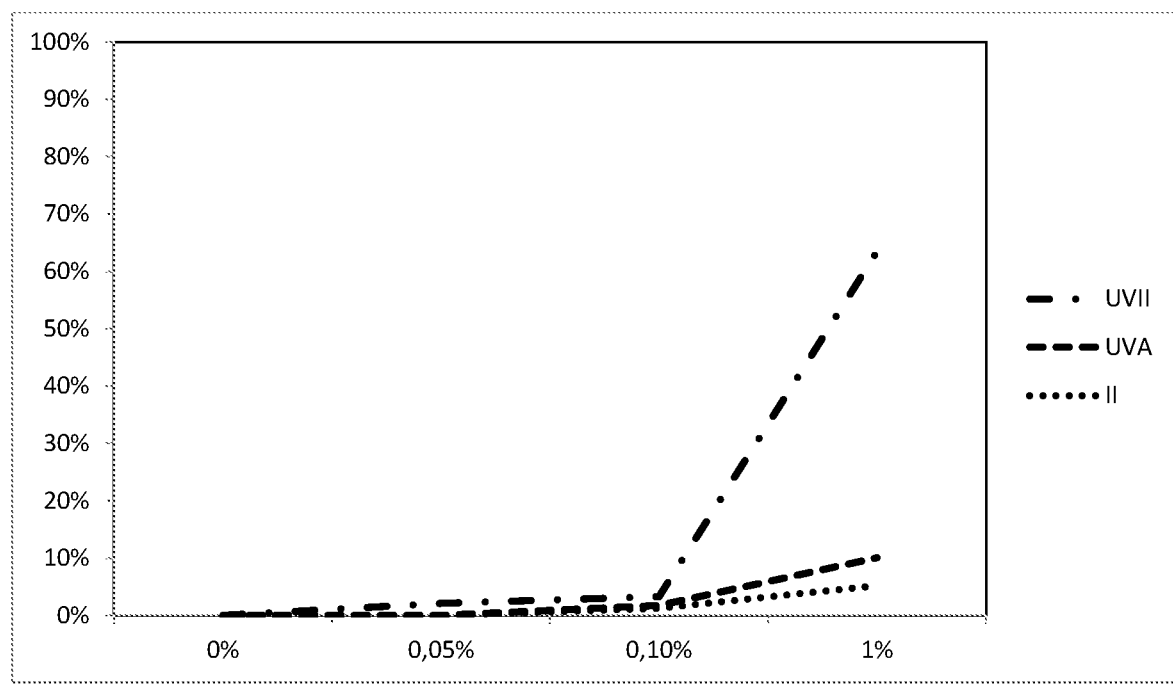
FIG. 21 shows a ratio (%) of necrotic versus living cells when exposed to the apparatus comprising UVA irradiation 2.76 J/cm2 and ionization irradiation concomitant with 0.5 Gy X-ray (II) in increased amounts of Bergamot enteric oil. The combination irradiation of UV and ionization with the apparatus of the invention (UVII) is denoted by a line of alternating lines and dots (highest line), UVA irradiation is denoted by a dotted line and ionization irradiation (II) is denoted by dotted line (middle line) with smaller dots (lowest line).

The ratio of necrotic versus living cells were counted with a microscope. Apoptotic cells or cell bodies were excluded from counting. The results are shown in Table 1 and FIG. 21.

TABLE 1

The ratio of necrotic versus living cells when exposed to UVII, UVA 2.76 J/cm² concomitant with 0.5 Gy X-ray from an apparatus comprising Verifix UVA-star 500 and Opti 150/30/50HC-100. The control ratio is subtracted from the analysis.

|  | n | mean | minimum | maximum | St-Dev |
|---|---|---|---|---|---|
| UVII | 2 | 0.317 | 0.213 | 0.421 | 0.147 |
| UVA or II | 4 | 0.038 | 0.069 | 0.122 | 0.098 |

T-test showed that T-value was 2.86
n = 4
P = 0.046

Abbreviations
CT=computed tomograph
UV=Ultraviolet light/irradiation type NBUVB=Narrowband UVB
PUVA=UVA administered after that the patient or the animal has been given psoralen administered orally or topically where the UV-light thereafter hits the skin.
PUVA-sol=PUVA with the sun as a light source
GVHD=Graft-versus-host-disease or Transplantation versus host reaction Definition The terms "irradiation" and "radiation" are both used describe processes of transferring energy to and from an object including the transfer of energy via electromagnetic waves or the emission of particles during nuclear decay, and further including a process by which an object may be exposed to radiation.

The term "object" is understood to mean a mammal body, such as a human or animal body, as well as a part of a body, or a non-mammal body, such as a surface or a fluid.

REFERENCES

Banath P. 1998 "Rejoining of DNA single- and double-strand breaks in human white blood cells exposed to ionization irradiation", International Journal of Irradiation Biology, Vol. 73 No. 6, p. 649-660

Barry S. et al. 1976 "Molecular and genetic basis for furocoumarin reactions", Mutation Research, Vol. 39 p. 29-74

Cardo C. et al. 2007 "Pathogen inactivation of Trypanosoma cruzi in plasma and platelet concentrates using riboflavin and ultraviolet light", Transfusion and Apheresis Science Vol. 37 p. 131-137

Heering W. 2004: "UV-sources—Basics, Properties and Applications", IUVA NEWS, Vol. 6, No. 4, p. 7-13.

Hiraku Y. et al. 2007 "Photosensitized DNA Damage and its Protection via a Novel Mechanism", Photochemistry and Photobiology Vol 83 p. 205-212

Kitamura N. et al 2005 "Molecular aspects of furocoumarin reactions: Photophysics, photochemistry, photobiology, and structural analysis, Journal of Photochemistry and Photobiology" Photochemistry Reviews Vol. 6 p. 168-185

Kumar C. et al. 2016 "Relevance of radiobiological concepts in radionuclide therapy of cancer", International Journal of Irradiation Biology, DOI: 10.3109/09553002.2016.1144944

Nocentini S. 1999 "Rejoining kinetics of DNA Single- and Double stranded breaks in normal and DNA ligase-deficient cells after exposure to Ultraviolet C and gamma irradiation: An evaluation of ligating activities involved in different DNA repair processes", Irradiation research Vol. 151, p. 423-432.

Parrish J. A. et al. 1974: "Photochemotherapy of psoriasis with oral methoxsalen and long-wave ultraviolet light", The New England Journal of Medicine Vol. 291 p. 1207-1211.

Parrish J. A., Jaenicke K. F. 1981: "Action spectrum for phototherapy of psoriasis", J Invest Dermatology Vol. 75 No. 5 p. 359-362.

Pathak M. A. et al. 1951: "The Presently Known Distribution of Furanocoumarins (Psoralens) in plants", Journal of Investigative Dermatology p. 225-239

Pourakbar M. et al. 2016 "Homogenous VUV advanced oxidation process for enhanced Degradation and mineralization of antibiotics in contaminated water", Ecotoxicology and Environmental Safety Vol. 125 p. 72-77

Seghatchian J. 2012 "Characteristics of the THERAFLEX UV-Platelets pathogen inactivation system—An update" Transfusion and Apheresis Science vol. 46 p. 221-229

Singh T. P. et al 2011 "8-methoxypsoralen plus ultraviolet A therapy acts via inhibition of the IL-23/Th17 axis and induction of Foxp3+ regulatory T cells involving CTLA4 signaling in a psoriasis-like skin disorder" J Immunol; vol. 184 no. 12 p. 7257-67

Srinivas C. R. and Pai S. 1997: "Psoralens", Indian J Dermatol Venereol Leprol Vol. 63 p. 276-287.

Stern R. S. 2007: "Psoralen and Ultraviolet A Light Therapy for Psoriasis", The New England Journal of Medicine Vol. 357 No. 7 p. 682-690

Wiskeman A. 1978: "UVB-phototherapy of psoriasis using a standing box developed for PUVA-therapy", Z Hautkr Vol. 53, No. 18, 633-636

Wolf P. et al. 2016 "Serotonin signaling is crucial in the induction of PUVA-induced systemic suppression of delayed type hypersensitivity but not local apoptosis or inflammation of the skin", Exp. Dermatology, Epub ahead of print Wu J. et al. 2009 "Optimization of the comet assay for the sensitive detection of PUVA-induced DNA interstrand cross-links", Mutagenesis vol. 24 no. 2 p. 173-181

The invention claimed is:

1. An apparatus (1) for use in irradiation therapy, comprising
a first light source configured for emitting X-ray or gamma-irradiation at a wavelength below 100 nm, and
a second light source configured for emitting ultraviolet (UV) light at a wave length between 100 and 450 nm;
wherein the first and second light sources are non-laser light sources wherein the first and second light sources are positioned in a circular, as semi-circular or juxtaposed with respect to each other and are aligned to cooperate for administrating even irradiation over a human body part simultaneously or alternately, such that irradiation from the first light source over the body part overlaps with irradiation from the second light source over the same body part; and a power source (4) and a control unit (5) configured to provide a user interface for controlling irradiations of said first and second light sources.

2. The apparatus according to claim 1, wherein the irradiation is emitted from the first and second light sources simultaneously and sequentially.

3. The apparatus according to claim 1, wherein an ionization irradiation (8) is photo irradiation or particle irradiation.

4. The apparatus according to claim 1, wherein the ionization irradiation (8) is at a wave length between 0.001 and 10 nm.

5. The apparatus according to claim 1, whereby the UV irradiation (9) is UVA irradiation at a wave length between 315 and 400 nm.

6. The apparatus according to claim 1, whereby the UV irradiation (9) is UVB irradiation at a wave length between 280 and 315 nm.

7. The apparatus according to claim 1, whereby the UV irradiation (9) is UVC irradiation at a wave length between 100 and 280 nm.

8. The apparatus according to claim 1, wherein the irradiation from the first light source is at a maximum power of 1.00 mGy/s and the irradiation from said second light source is at a minimum power of 0.2 mW/cm^2.

9. The apparatus according to claim 1, wherein the irradiation from the first light source is at a maximum power of 0.333 mGy/s and the irradiation from said second light source is at a minimum power of 3.8 mW/cm^2.

10. A method for radiating an object (7), comprising: providing an apparatus (1) comprising:
   a first light source configured for emitting X-Ray or gamma-irradiation at a wave length below 100 nm,
   a second light source configured for emitting UV light at a wave length between 100 and 450 nm,
   a power source (4) and a control unit (5) configured to provide a user interface for controlling irradiations of said first and second light sources,
   wherein the first and second light sources are non-laser light sources, wherein the first and second light sources are positioned in a circular, a semi-circular with respect to each other and are aligned to cooperate for administrating even irradiation over a human body part;
   emitting irradiation (8,9) from the first and second light sources simultaneously or alternately, for a period of time, such that irradiation from the first light source over the body part overlaps with irradiation from the second light source over the same body part.

11. A method for use of the apparatus (1) according to claim 1, comprising
   providing the apparatus (1) according to claim 1,
   positioning an object (7) to be irradiated on a surface,
   emitting irradiation from the first and second light sources simultaneously or alternately for a period of time between 1 minute and 48 hours,
   optionally repeat the emitting irradiation (8,9),
   optionally administering one or more photochemically active compound to the object (7) before or between irradiations.

12. The method according to claim 11, whereby the irradiation from the first and second light sources is simultaneous and sequential.

13. The method according to claim 11, whereby period of time for simultaneous irradiation is between 1 and 10 minutes and a non-irradiation period between sequential irradiations is between 5 minutes and 48 hours.

14. The method according to claim 11, whereby period of time for alternate irradiation is between 1 and 5 minutes for ionization irradiation and between 1 and 10 minutes for UV irradiation with a non-radiating period of between 5 minutes and 48 hours.

* * * * *